(12) United States Patent
Raso et al.

(10) Patent No.: US 11,553,881 B2
(45) Date of Patent: Jan. 17, 2023

(54) FLOATING CARDIAC ACTIVITY SENSOR FOR A SPORTS EQUIPMENT HANDLE

(71) Applicant: Polar Electro Oy, Kempele (FI)

(72) Inventors: Andrea Raso, Arbedo (CH); Niclas Granqvist, Mägenwil (CH); Patrick Celka, Neuchatel (CH); Sami Karvonen, Travers (CH); Stephane Berginz, Môtiers (CH)

(73) Assignee: Polar Electro Oy, Kempele (FI)

( * ) Notice: Subject to any disclaimer, the term of this patent is extended or adjusted under 35 U.S.C. 154(b) by 732 days.

(21) Appl. No.: 16/406,206

(22) Filed: May 8, 2019

(65) Prior Publication Data
US 2019/0350530 A1 Nov. 21, 2019

(30) Foreign Application Priority Data

May 17, 2018 (EP) ...................................... 8172842

(51) Int. Cl.
*A61B 5/00* (2006.01)
*A61B 5/024* (2006.01)

(52) U.S. Cl.
CPC ........ *A61B 5/6895* (2013.01); *A61B 5/02433* (2013.01); *A61B 5/6826* (2013.01); *A61B 5/6843* (2013.01); *A61B 2562/0219* (2013.01)

(58) Field of Classification Search
None
See application file for complete search history.

(56) References Cited

U.S. PATENT DOCUMENTS

| | | | | |
|---|---|---|---|---|
| 3,659,613 A | * | 5/1972 | Bredemeier | A61F 9/008 606/3 |
| 2016/0287108 A1 | * | 10/2016 | Wei | A61B 5/02427 |
| 2017/0238812 A1 | * | 8/2017 | Atlas | A61B 5/4818 |
| 2017/0347957 A1 | * | 12/2017 | van den Ende | H01L 41/09 |
| 2018/0235489 A1 | * | 8/2018 | Mouradian | A61B 5/02416 |
| 2018/0353134 A1 | * | 12/2018 | Walter | A61B 5/6844 |
| 2019/0008396 A1 | * | 1/2019 | Baron | A61B 5/14552 |
| 2019/0099095 A1 | * | 4/2019 | Zhang | A61B 5/7278 |
| 2019/0387972 A1 | * | 12/2019 | Hu | A61B 5/02438 |
| 2020/0390362 A1 | * | 12/2020 | Westerhof | A61B 5/0531 |

FOREIGN PATENT DOCUMENTS

| | | |
|---|---|---|
| CA | 2517184 A1 | 2/2007 |
| WO | 2015/029043 A1 | 3/2015 |
| WO | 2017/021923 A2 | 2/2017 |
| WO | 2017/027551 A1 | 2/2017 |

OTHER PUBLICATIONS

Ash et al., "Effect of wavelength and beam width on penetration in light-tissue interaction using computational methods". Laser Med. Sci, 2017, 32:1909-1918. (Year: 2017).*
Search Report issued in European Patent Application No. 18172842.9, dated Nov. 14, 2018.

* cited by examiner

*Primary Examiner* — Yi-Shan Yang

(74) *Attorney, Agent, or Firm* — FisherBroyles, LLP

(57) ABSTRACT

A cardiac activity measurement assembly for a sports equipment handle and the handle is disclosed, wherein the assembly includes an optical cardiac activity sensor configured to measure cardiac activity of a user, and an attachment element for floatingly attaching the optical cardiac activity sensor to a handle of sports equipment in order to reduce pressure on a measuring head of the sensor caused by a skin contact between the measuring head and at least one finger or a palm of the user when gripping the handle.

14 Claims, 11 Drawing Sheets

FLOATING CARDIAC ACTIVITY SENSOR FOR A SPORTS EQUIPMENT HANDLE

CROSS-REFERENCE TO RELATED APPLICATION

This application claims the benefit of European Patent Application No. 18172842.9, filed on May 17, 2018, the disclosure of which is incorporated herein by reference in its entirety.

BACKGROUND

Field

The invention relates to measuring cardiac activity. More particularly, the present invention relates to solutions which enable cardiac activity measurement by sensor(s) situated at sports equipment.

Description of the Related Art

In the past, cardiac activity has been measured using electrode based measurement system. However, it may not be the best option in some cases. Hence, there may be room for developing new kind of arrangements that are embedded into sports equipment for measuring the cardiac activity.

SUMMARY

According to an aspect, there is provided a cardiac activity measurement assembly for a sports equipment handle, wherein the assembly includes an optical cardiac activity sensor configured to measure cardiac activity of a user, and attachment element for floatingly attaching the optical cardiac activity sensor to a handle of sports equipment in order to reduce pressure on a measuring head of the sensor caused by a skin contact between the measuring head and at least one finger or a palm of the user when gripping the handle.

According to another aspect, there is provided a handle for sports equipment, wherein the handle includes a cardiac activity measurement assembly, and the assembly includes an optical cardiac activity sensor configured to measure cardiac activity of a user, and attachment element for floatingly attaching the optical cardiac activity sensor to the handle in order to reduce pressure on a measuring head of the sensor caused by a skin contact between the measuring head and at least one finger or a palm of the user when gripping the handle.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
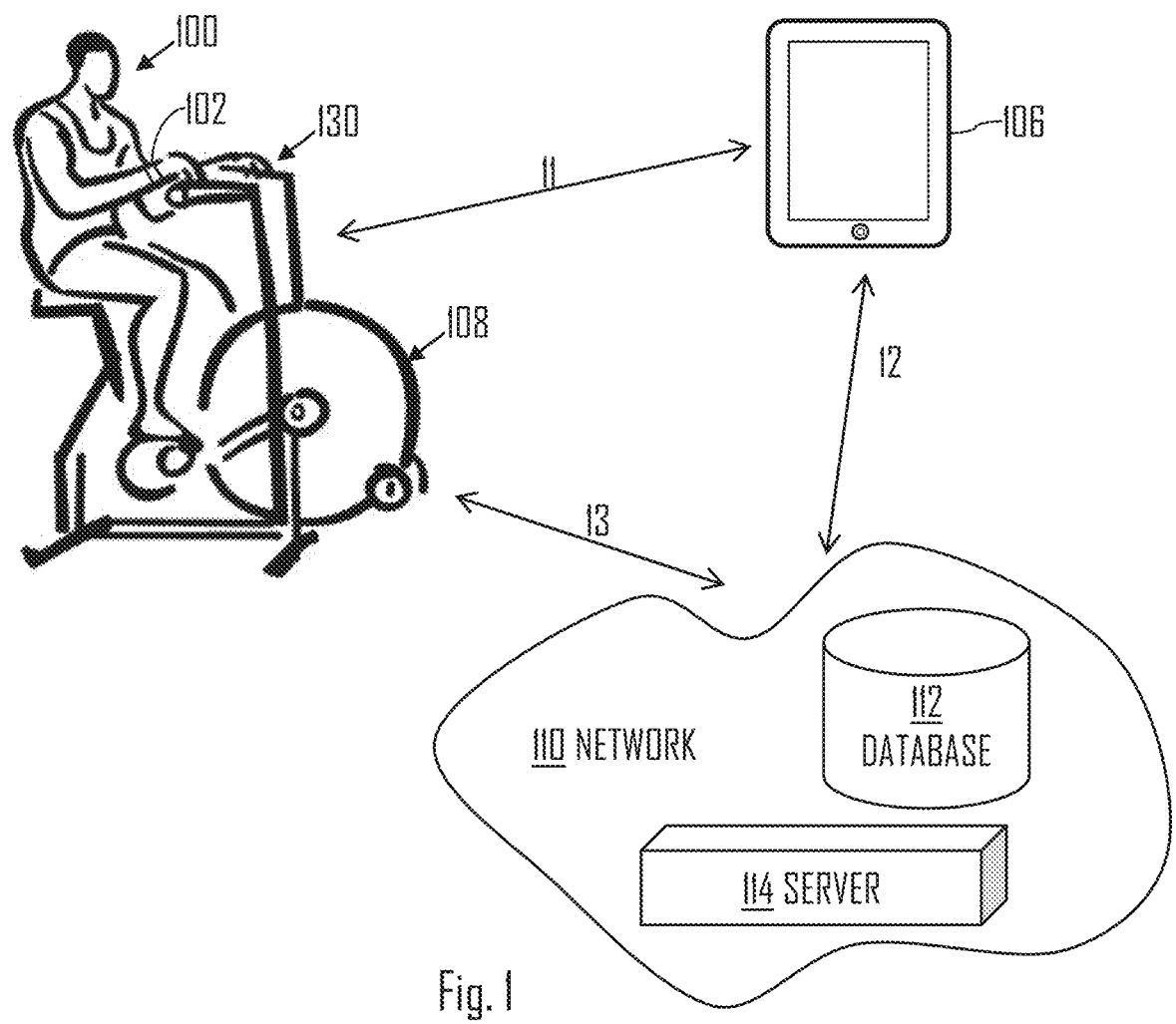
FIG. 1 illustrates an example system to which embodiments may be applied.

FIG. 1 illustrates a system to which embodiments of the invention may be applied. Said system may be used to monitor physical training, activity, and/or inactivity of a user 100. The system may be a performance monitoring system for measuring performance of the user 100 during training. For example, the system may be a gym system or arrangement in a gym environment. Referring to FIG. 1, the user 100 (can be referred to as exerciser) carries out a physical exercise in a gym, fitness center, home, or in a similar training environment by using a gym apparatus, sports device or sports equipment 108, such as a treadmill, an exercise cycle, a rowing machine, elliptical, a skiing training machine, a racket (e.g. tennis), a stick (e.g. hockey), or a pole (e.g. skiing pole). Now, there are different ways to monitor physical performance in such environment. For example, the user 100 may wear a wearable device, such as a wrist device 102. Due to simplicity reasons, let us now describe the wearable device as being the wrist device 102. However, at least some embodiments described in relation to wrist device 102 may be utilized by other wearable devices. The wrist device 102 may be, for example, a smart watch, a smart device, sports watch, and/or an activity tracking apparatus (e.g. bracelet, arm band, wrist band, mobile phone, glasses). In an embodiment, the wrist device 102 is an activity tracking apparatus. This may mean that said apparatus may be worn in other parts of the user 100, such as but not limited to forearm, bicep area, neck, forehead, and/or leg. For example, the wrist device 102 may comprise cardiac activity sensor and/or receive cardiac activity measurement data from external sensors. Hence, performance of the user may be monitored.

In another example, additionally or alternatively, the sports apparatus 108 comprises a cardiac activity sensor 130 for measuring cardiac activity of the user 100. In the system, different devices (e.g. 102, 130, 106, 108, 112, 114) may be connected with each other (i.e. with one or more of the devices) via connections 11, 12, 13. The connections 11, 12, 13 may be wireless or wired, and can be used, for example, to transmit data related to the cardiac activity measurement. Thus, for example, the measurement may be performed by sensor 130 and the results displayed on wrist device 102, on portable electronic device 106 (e.g. smart phone, tablet computer, computer), and/or on a display of the sports apparatus 108 (if such is available). The data transfer may be based on Bluetooth protocol, for example. Other wireless communication methods, such as Wireless Local Area Network (WLAN) and/or Near Field Communication (NFC), may also be used. In case of communicating directly with a cellular network, the wrist device 102, the sensor 130, or the sports apparatus 108 may comprise similar communication capabilities as mobile devices, such as 2G, 3G, LTE, LTE-A, 4G and/or 5G communication capabilities. Thus, for example, said devices may comprise the communication circuitry capable of operating on said technologies, a Subscriber Identification Module (SIM) and/or a memory comprising a virtual SIM configured to provide a secured identification when operating with the cellular network. So, there may be different ways how to measure, process and monitor cardiac activity of the user 100 in the described system. The benefit of such arrangement is that the user 100 may monitor his/her performance in order to develop according to an activity plan, for example.

Normally, the cardiac activity sensors (e.g. sensor 130) being integral part of the apparatus 108 are based on electrode measurement technology. However, reliability of electrode measurement may decrease during rigorous physical activity or in presence of strong motion artifacts. Hence, it is now proposed that optical measurement is, additionally or alternatively, used for measuring the cardiac activity of the user 100. Therefore, there is provided a cardiac activity measurement assembly for a sports equipment 108 handle, said assembly comprising: an optical cardiac activity sensor configured to measure cardiac activity of the user 100; and attachment element for floatingly attaching the optical cardiac activity sensor to a handle of a sports equipment 108 in order to reduce pressure on a measuring head of said sensor caused by a physical contact (can be referred to as skin contact or body tissue contact in context of the present application) between said measuring head and at least one finger or a palm of the user when gripping (or holding or pressing) the handle.

That is, during sport session the handle(s) (sometimes referred to as grip or handle bar) of the sports equipment 108 may be quite strongly squeezed leading to unwanted artifacts. Another problem is that with a given pressure the signal amplitude may drop and become unusable because capillaries and arterioles block and do not let or at least reduce the blood flow. Exploiting the floating attachment of the optical cardiac activity sensor, a part of the force applied between the finger or the palm and the sensor may be absorbed so that the pressure on the finger or the palm (and also on the sensor) is reduced, and the quality of the signal is good enough to detect cardiac activity even on intense activity.

In the context of the proposed solution, cardiac activity may refer to heart activity, heart rate (HR), ECG (Electrocardiogram), instantaneous heart rate values, average heart rate values averaged over a determined number of heart beats, RR intervals acquired from peak intervals of heart rate signals, Heart Beat Interval (HBI), and/or Heart Rate Variability (HRV). It is noted that the sensor 130 may measure the cardiac activity and provide raw measurement data to one or more processing devices for processing the raw measurement data into said one or more metrics (e.g. HR, HRV, HBI). For example, the sensor 130 may provide measurements to processing device of the sports equipment 108 or to the wrist device 102, wherein said devices processes the measurements into metrics which may be further processed and/or displayed to the user. For example, the sports equipment 108 may comprise an interface unit which may comprise a user interface to display e.g. the received cardiac activity measurement data to the user 100. The interface unit may comprise input buttons enabling the user to configure the sports equipment 108 and control the execution of the physical exercise. The user interface may also comprise a touch-sensitive display, for example. The interface unit may further act as a gateway and direct the cardiac activity data to a remote computer 114 such as a local or a web server via a network 110, or to the wrist device 102 via local connection (e.g. Bluetooth). Said data may be stored to a training database 112 and associated with an identifier of the user 100, for example.

The optical cardiac activity sensor 130 may be referred to as PPG (photoplethysmography) sensor, for example. For example, the optical cardiac activity sensor 130 may detect the cardiac activity of the user 100 by optical measurement, which may comprise sending a light beam towards skin of the user 100 and measuring the bounced and/or emitted light from the skin of the user 100. The light beam may alter when travelling through veins of the user 100 and the alterations may be detected using the measurements by the optical cardiac activity sensor (sometimes referred also as optical heart rate (OHR)) 130.

Figure 2A:
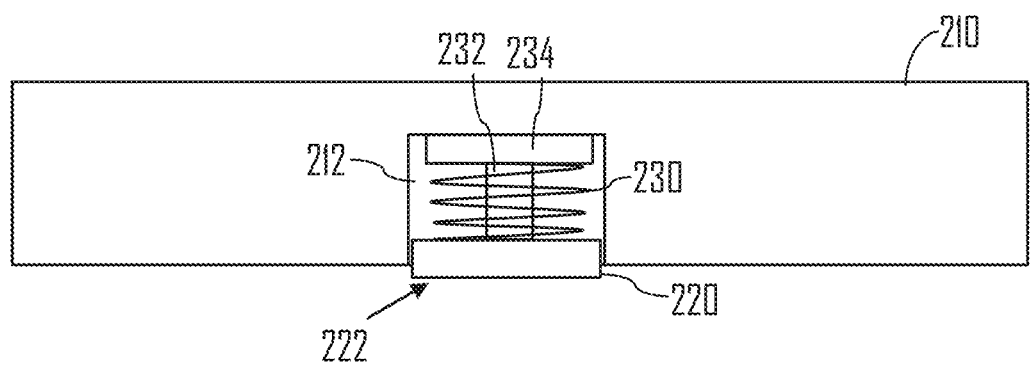
FIGS. 2A, 2B, 2C, 2D, 2E, 2F, and 2G illustrate some embodiments.
Figure 2B:
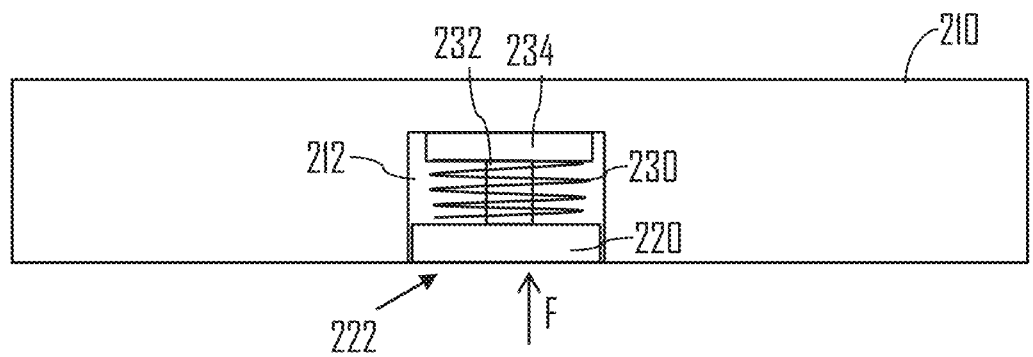

Let us then look a bit closer on different embodiments of the proposed solution with help of the attached drawings. FIGS. 2A and 2B illustrate floating attachment of the optical cardiac activity sensor according to a first embodiment, FIG. 2C according to a second embodiment, and FIG. 2D according to a third embodiment. Further embodiment is illustrate in FIG. 2H. It is further noted that said embodiments may be mixed with each other at least in some examples.

Referring first to FIGS. 2A and 2B, the attachment element for floatingly attaching an optical cardiac activity sensor 220 (i.e. similar or same as sensor 130) to a handle 210 of a sports equipment 108 comprises at least one spring 230, such as at least one mechanical spring 230 which is used as an example. Thus, as force F (see FIG. 2B) is applied to a measuring head 222 of the sensor 220 (force is towards the handle), the spring 230 may compress and thus the counterforce provided by the spring may increase. At some point, the force F is equal to the spring force (i.e. the counterforce) and thus the measuring head 222 may be in force equilibrium state. So, the force applied by the user 100 to the measuring head 222 may cause a pressure to the measuring head 222 which may be reduced by using the spring 230, for example. The force F may be caused by user gripping the handle, for example. Thus, for example, his/her finger(s) may press the measuring head 222.

According to an embodiment, the cardiac activity measurement assembly comprises a cavity 212 for receiving the optical cardiac activity sensor 220. For example, the spring 230 may be attached to a base 234 which may be attached to an inner wall (e.g. bottom wall of the cavity 212) of the cavity 212 as shown in FIGS. 2A and 2B. The cavity 212 may be comprised in the handle 210 or in a separate element of the assembly, wherein said separate element may be attached to the handle 210. Hence, the floating attachment may be achieved directly to a specific handle or by providing a base element which can be attached to any handle.

In an embodiment, the attachment element comprises one or more guide pins for guiding the movement of the optical cardiac activity sensor 220. In one example, such guide pin may be a spring bolt 232. However, different kinds of guide elements may be used. For example, the guide pin(s) may be used to reduce/prevent tilting of the measuring head 222 due to the force F and/or the spring force.

Figure 2C:
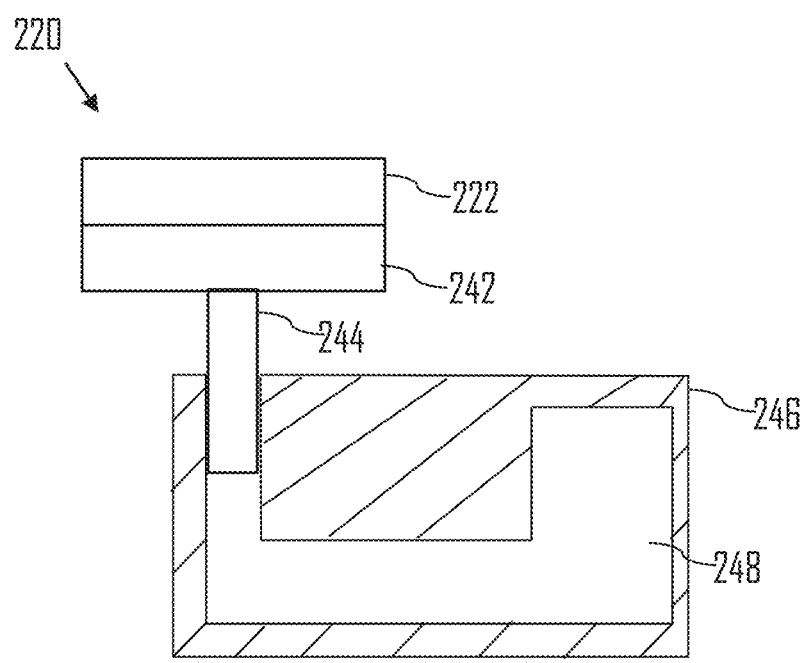

Referring to FIG. 2C, the attachment element comprises a hydraulic control system 242, 244, 246, 248. For example, the sensor's 220 measuring head 222 may be attached to a support 242 that has an elongation 244. The elongation 244 may be arranged to fit into an opening of a chamber 248. The chamber may be situated in a mechanic support 246. The mechanic support 246 may be attached to the handle 210, for example. The chamber 248 may have fluid, such as oil. Thus, a hydraulic counterforce may be caused by the hydraulic control system in response to a force to the measuring head 222 towards the support 242.

Figure 2D:
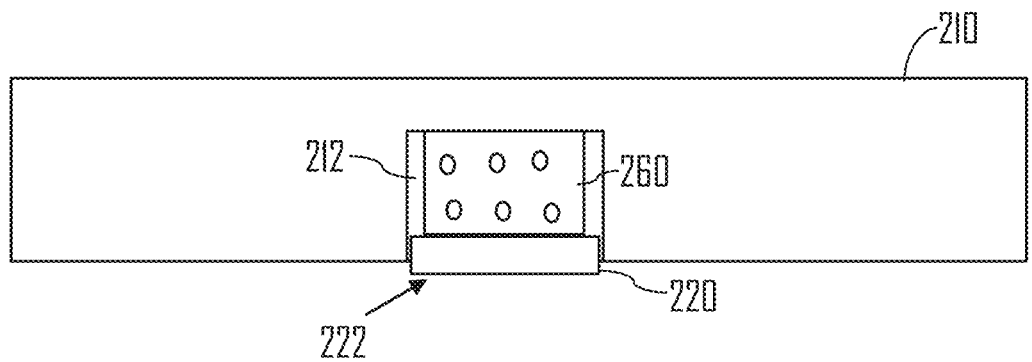

Referring to FIG. 2D, the situation may be similar as in FIGS. 2A and 2B. However, instead of a mechanical spring, the attachment element comprises elastic shock-absorbing material 260. The material may comprise, for example, rubber, synthetic rubber, and/or foam. It is noted that the attachment element may utilize both a spring or springs and elastic shock-absorbing material in some embodiments.

Figure 2E:
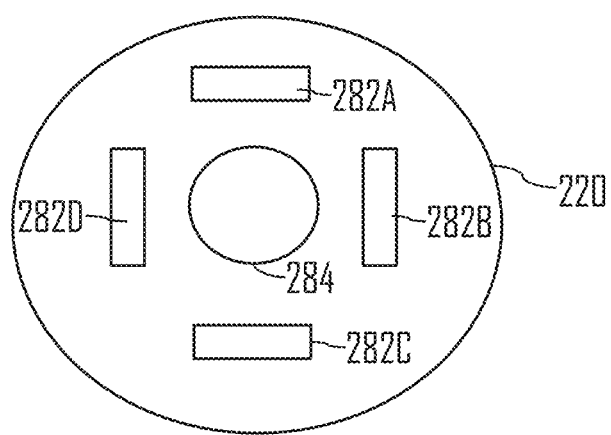
Figure 2F:
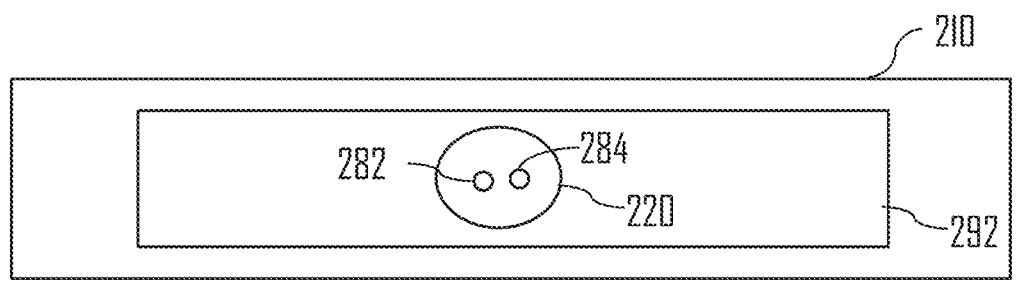

FIGS. 2E and 2F illustrate some embodiments. Referring to FIG. 2E, the sensor 220 may comprise one or more detectors 284 and one or more radiation elements 282A-D (can be referred to simply as 282). The detector(s) 284 are configured to detect radiation emitted by the radiating elements 282A-D. For example, the radiation may be visible light, ultraviolet and/or infrared.

Referring to FIG. 2F, the cardiac activity measurement assembly may further comprise at least one electrode 292 configured to be placed or arranged at the handle 210. Thus, for example, cardiac activity may be measured using both the optical and electrode based measurements. If more than one handle is used, at least two electrodes may be used (i.e. one at each handle) to measure cardiac activity. Later it is discussed how sensor fusion may be utilized in cases where there are at least two different measurements regarding the same metric.

Figure 2G:
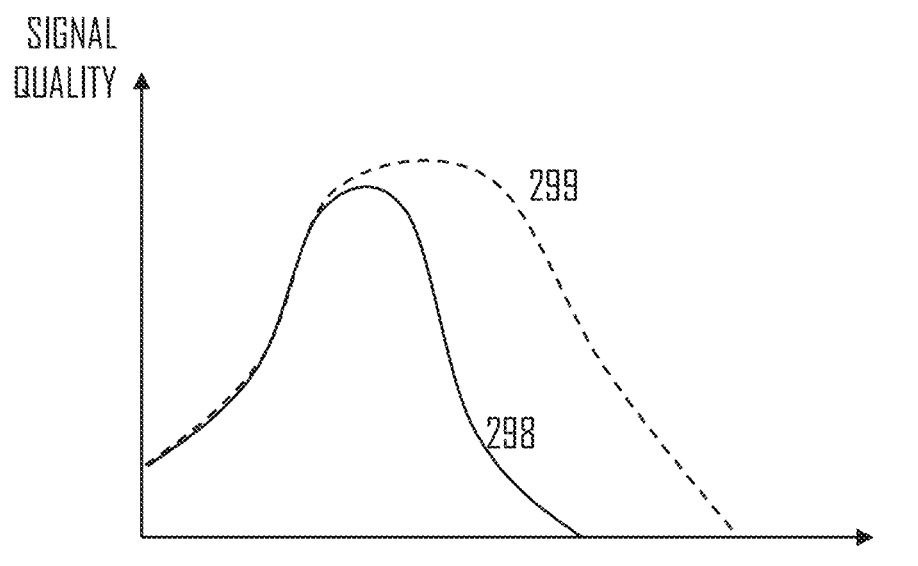

FIG. 2G illustrates examples about signal quality of the cardiac activity measurement. Referring to FIG. 2G, curve 298 may illustrate optical cardiac activity measurement that does not utilize the floating attachment mechanism which was introduced above. Curve 299 may illustrate optical cardiac activity measurement that utilizes the proposed solution. It is noted that at least in cases where the applied force (e.g. gripping force when gripping the handle) increases beyond a threshold, the non-floating mechanisms is not able to provide high enough signal quality. Hence, for example, cardiac activity metrics cannot be calculated from the measurements in a reliable manner. However, as the floating attachment is able to absorb some of the force, pressure can be standardized (or at least partly) and thus signal quality can be better even if more force is applied. In a way, the floating attachment mechanism can be seen as a way to standardize pressure on the measuring head 222 to enhance signal quality.

Figure 2H:
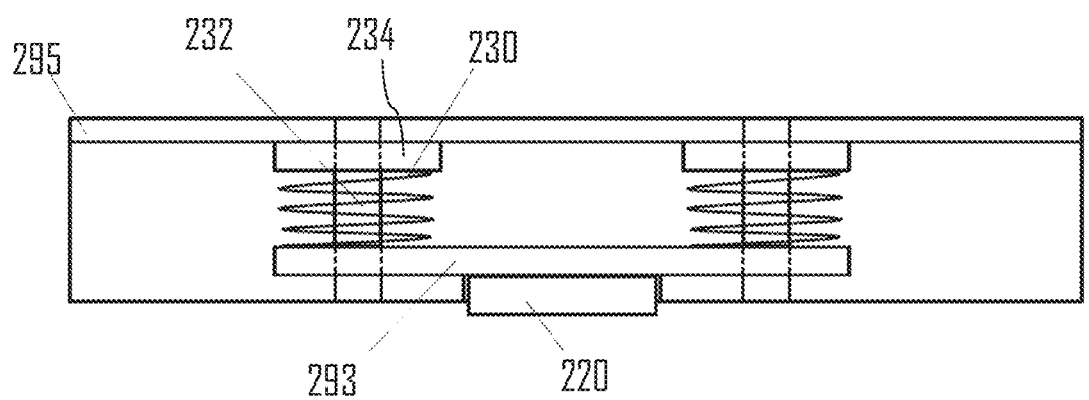
FIG. 2H illustrates an embodiment utilizing more than one spring to achieve the floating sensor structure.

FIG. 2H illustrates a further example embodiment. Referring to FIG. 2H, the system may be similar as in FIGS. 2A and 2B. However, now it is explicitly shown that more than one spring 230 (e.g. mechanical spring) can be used (only one is indicated with reference signs in the Figure). Additionally, it is shown that the arrangement may comprise a support 293 to which the sensor 220 and the springs 230 may be attached to. The support 293 may be used to link the spring force of said two or more springs 230 such that the springs 230 do not necessarily need to be attached directly to the sensor 220. However, such arrangement is also possible. As shown in FIG. 2H, the support may be attached to the spring bolts (or can be referred to as cylinder screw) 232 of the respective spring. Reference sign 295 may denote bottom or base of the handle bar 210. Such bottom or base is not shown in other floating attachment arrangement, but can still be used in each of the described solutions.

In an embodiment, the floating attachment mechanism (e.g. spring(s), hydraulic system, and/or elastic shock-absorbing material) is controllable. This may mean, for example, that the counterforce may be controlled. For example, stiffness of the spring may be increased or decreased or the hydraulic system parameters controlled. Such controlling is known in the fields of hydraulics, springs and other attachment mechanisms. Hence, the counterforce provided by the floating mechanism can be adjusted to be suitable for different users (e.g. different gripping methods and/or force), different handles and/or different installment locations on the handle. For example, if the sensor 220 is against palm of the user, the force may be greater than in cases where the sensor is against finger of the user. That is, the user may lean with this body towards the handle and thus cause force to the handles with his/her palms. On the other hand using, for example, a rowing machine, the pulling force may cause greater force to be inflicted to finger based sensors. Hence, it is noted that such adjustment mechanism may make the cardiac activity measurement assembly even better suitable for different use cases.

Figure 3A:
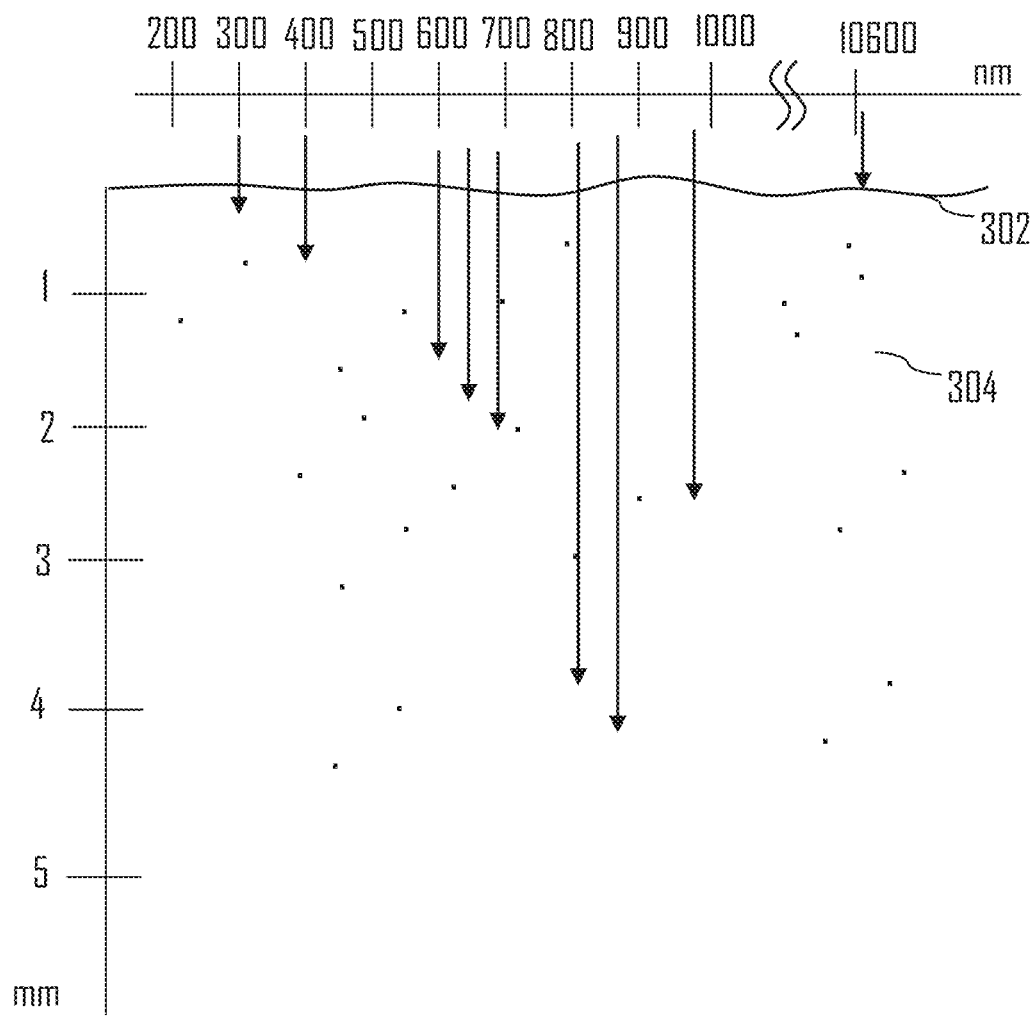
FIGS. 3A, 3B, 3C, and 3D illustrate some embodiments.
Figure 3B:
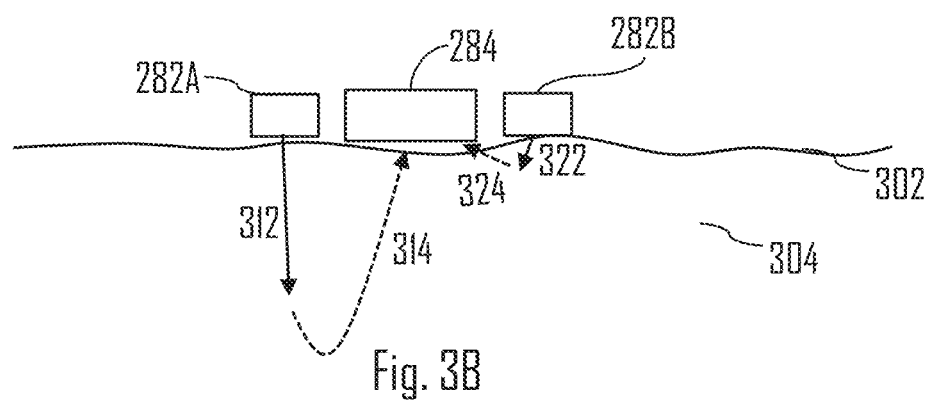

In some embodiments, the optical cardiac activity sensor 220 is configured to emit electromagnetic radiation of at least two different wavelengths. For such purpose the sensor 220 may comprise two or more radiation elements 282 (e.g. one or more light emitting elements (LEE), such as light emitting diodes (LED)). For example, different color LEEs (e.g. blue, green, yellow and/or red) can be used for the measurement. It is noted that in some cases the floating attachment mechanism may still not be enough to provide needed signal quality, and hence the cardiac activity measurement assembly for the sports equipment may utilize additional techniques for signal quality enhancement. One example of such may be the use of different wavelengths. FIGS. 3A and 3B illustrates some such embodiments.

Referring to FIG. 3A, relation between wavelength (nm, i.e. nanometers) of electromagnetic radiation and body tissue penetration depth (mm, i.e. millimeters) is shown. Body tissue 304 may be illustrated having a surface 302. As shown in the Figure, visible light may penetrate deeper into the body tissue 304 than ultraviolet (UV) and infrared (IR) radiation having wavelength above 10000 nm. Particularly, wavelengths between 100 nm and 400 nm and over 10000 nm seem to be such that the radiation does not penetrate the surface 302 or at least does not penetrate deep into the body tissue 304. That is, does not reach dermis which is from about 1 mm to 3 mm. Furthermore, if the body tissue is sweaty, reflection may happen on other areas of the spectrum. For example, 975 nm may be an example of such wavelength that reflects and does not penetrate the surface 302 if the body tissue (i.e. skin) is sweaty.

Referring now to FIG. 3B, the optical cardiac activity sensor 220 is configured to emit a first electromagnetic radiation 312 having a first wavelength for measuring the cardiac activity of the user and a second electromagnetic radiation 322 having a second wavelength for measuring motion between the measuring head 222 and the body tissue 304 of the user. So, force example, the element 282A may be an LEE (e.g. LED) which transmits visible light 312. The alterations of that light 314 may be detected by the detector 284. Hence, cardiac activity may be measured as known in the art. However, now another radiation element 28B may be used to transmit electromagnetic radiation 322 (e.g. IR, UV or water absorption spectra) which may reflect 324 from the surface 302 (or from top layers of the body tissue 304) and further be detected by the same detector 284 and/or by a different detector. Thus, motion artefacts may be measured and their effect reduced/removed from the cardiac activity measurement data obtained using the visible light 312. That is, the first wavelength may be such that the first electromagnetic radiation 312 penetrates deeper into the body tissue compared with the second electromagnetic radiation 322.

In an embodiment, the first electromagnetic radiation 312 comprises visible light and the second electromagnetic radiation 322 comprises ultraviolet and/or infrared radiation. As noted above, wavelengths between 200-400 nm (especially about 200 nm) and over 10000 nm may be suitable for measuring the motion. In an embodiment, the second electromagnetic radiation 322 is IR and/or UV radiation, or at least majority of said radiation is IR and/or UV.

Figure 3C:
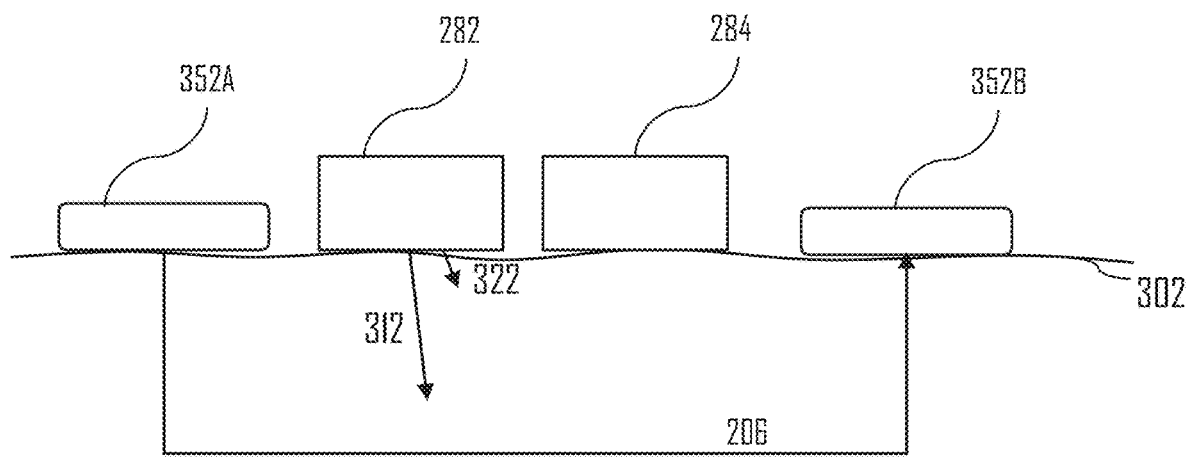
Figure 3D:
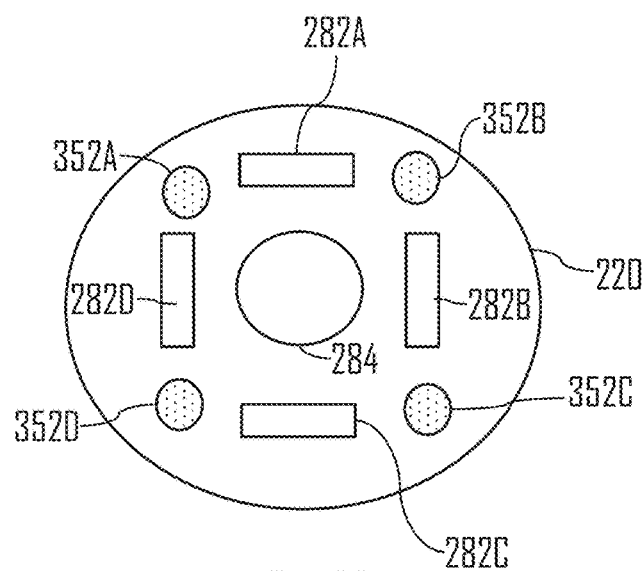

FIGS. 3C and 3D illustrates some alternative or additional ways to measure motion of the measurement head 222 with respect to the body tissue 304. Referring to FIGS. 3C and 3D, the cardiac activity measurement assembly may further comprise a plurality of electrodes 352A-D (e.g. two or four electrodes) situated at the measuring head 222 of the optical cardiac activity sensor 220 and configured to measure motion between the measuring head 222 and the body tissue 304 of the user. The electrodes enable bioimpedance measurement on a measurement area to obtain a bioimpedance signal. The measurement area may refer to the area at which the optical measurement is performed. Thus, cardiac activity signal and bioimpedance signal may be obtained are may be associated with the same measurement area. The measurement area may be comprised in the body tissue 304 of the user 100. Arrow 206 may indicate a bioimpedance measurement path between the electrodes 352A and 352B (other paths may additionally be utilized if more than two electrodes are used). The electrodes 352A-D may be arranged and placed such that they can be used to obtain the bioimpedance signal representing and/or indicating bioimpedance of the measurement area. The path 206 may even cross the emitted light 312 and/or the detected light. Changes in the bioimpedance signal may be detected which may be caused by a motion artefact(s). That is, the motion artefacts may cause the cardiac activity measurement to be inaccurate.

Hence, according to an embodiment, the cardiac activity measurement assembly further comprises a processing circuitry configured to obtain motion data indicating the motion between the measuring head and the body tissue of the user and cardiac activity data from the optical cardiac activity sensor, and to process the cardiac activity data based on the motion data in order to reduce effect of motion artefacts in the cardiac activity data. The motion data may be obtained using one or more of the discussed methods. For example, UV or IR light may be used to obtain a motion signal and/or the bioimpedance measurement may be used to obtain a motion signal. Hence, it is possible to utilize one or both motion signals to reduce the motion artifact effect on the cardiac activity measurement and/or the cardiac activity data obtained on the basis of the measurement.

According to an embodiment, the motion measurements are for determining quality of a physical contact between body tissue 304 of the user and the sensor 220. Based on the quality determination, an action may be performed. Such action may comprise indicating the quality to the user via user interface, selecting a sensor amongst a plurality of sensors (e.g. if more than one sensor source is available, best source(s) or source(s) which are associated with quality exceeding a threshold are used), and/or changing sensor configuration (e.g. selecting wavelength for cardiac activity measurement and/or for motion measurement), to name a few examples. Another example is discussed later in which the quality of contact may be used to determine weighting factor for sensor fusion algorithm.

Looking at FIG. 3D, in an embodiment, the measuring head 222 and/or the sensor 220 has a diameter between 15-30 millimeters (mm), preferably between 20-27 mm. Hence, as it may be embedded into a recess in the handle 210, the recess may be such (i.e. substantially the same diameter as the sensor, but such that the sensor fits into the recess) that user's finger is not able to too deep into said recess. Thus, injury risk can be reduced. The recess may refer to the cavity 212.

Figure 4:
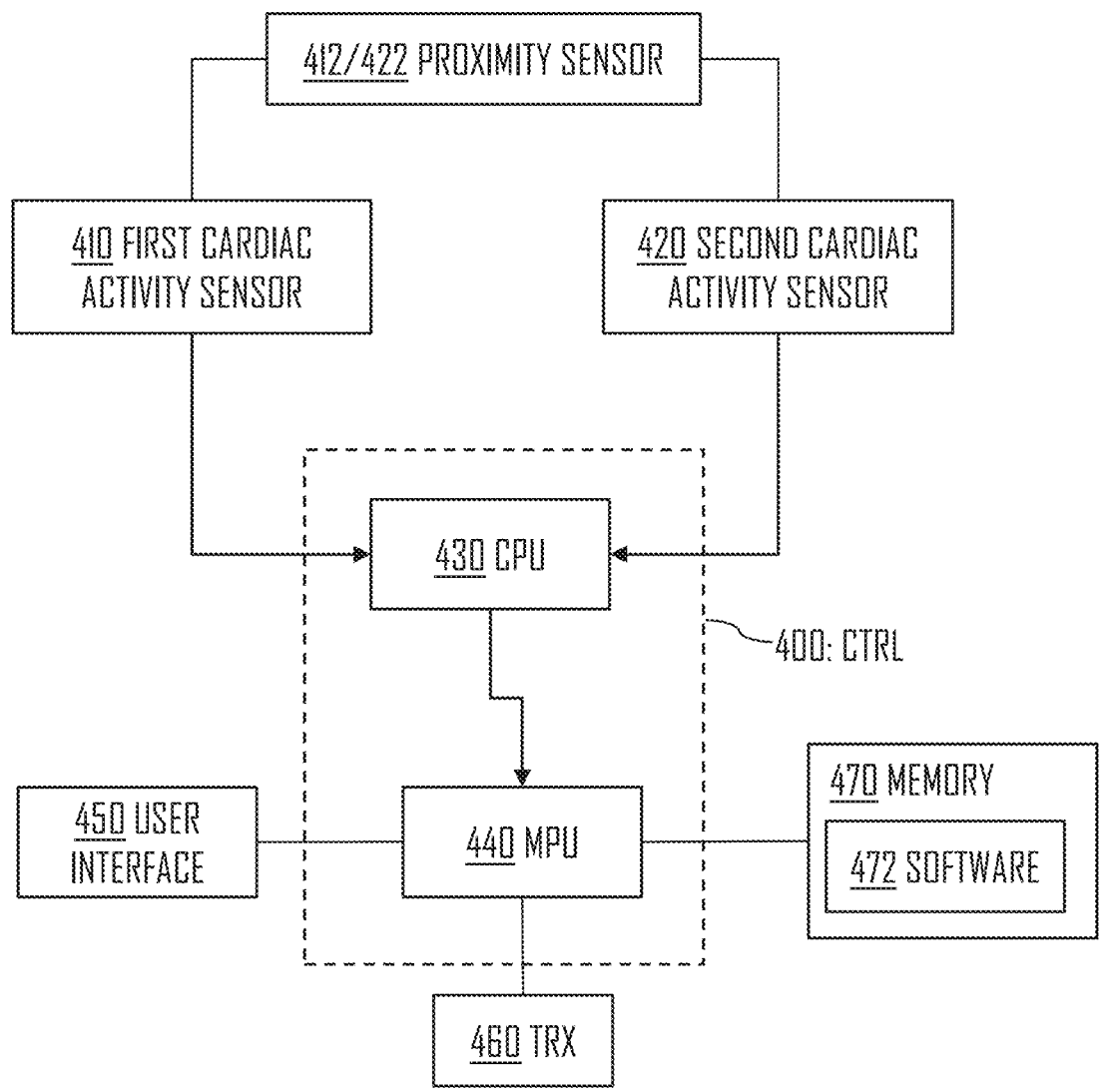
FIG. 4 illustrates a block diagram of a cardiac activity measurement arrangement according to an embodiment.

Let us then look closer on FIG. 4 illustrating a block diagram according to an embodiment. Referring to FIG. 4, the cardiac activity measurement assembly may further comprise a controller (CTRL) 400 for causing and/or performing the actions of the described assembly. For example, the CTRL 400 may receive cardiac activity measurements from one or more optical sensors (e.g. 220) and/or electrodes. Further, the CTRL 400 may obtain motion measurements (sometimes simply referred to as motion data) based on bioimpedance measurement, electromagnetic radiation (e.g. UV, IR, and/or reflection due to moisture, such as sweat), and/or motion circuitry measurement (e.g. one or more accelerometer and/or one or more gyroscopes). The motion measurements may indicated movement/motion between the sensor 220 (or more particularly the measuring head 222) and body tissue of the user. Such measurements may thus be used to determine motion artifacts in each cardiac activity signal and to process said cardiac activity signals such that the motion artifacts are removed or at least mitigated. The CTRL 400 may thus be configured to process said measurements into cardiac activity metric and to output the metric(s) to the user. The CTRL 400 may be comprised in the sports equipment 108, for example. However, it is possible that at least some of the actions are shared between different entities, such as the sports equipment 108, server 114, and/or wrist device 102.

According to an embodiments, the CTRL comprises a central processing unit (CPU) 430 communicatively coupled with one or more cardiac activity sensors 410, 420 (e.g. both similar or the same as sensor 220, or in some embodiments one may be an electrode based sensor and the other similar as sensor 220). The CPU 430 may be coupled to other sensors as well (e.g. cardiac activity electrodes and/or bioimpedance electrodes). The CPU 430 may preprocess the cardiac activity data and/or motion data and provide it to a main processing unit (MPU) 440 for further processing. For example, the CPU 430 may be placed closer to the handle(s) of the sports equipment and perform initial processing (e.g. steps 514, 516 of FIG. 5), and wherein the MPU 440 is configured to perform more sophisticated processing, such as calculating one or more metrics from the obtained signal (s).

Said assembly may further comprise a user interface 450 and a communication circuitry (TRX) 460 as discussed above. These may be communicatively coupled with the CTRL 400 in order to output (e.g. display, audio, transmission) data/parameter(s) related to cardiac activity of the user. In an embodiment, the CTRL 400 comprises at least one processor, wherein the assembly further comprises at least one memory 470 including a computer program code (i.e. software) 472, wherein the at least one processor and the computer program code are configured to cause the CTRL 400 to perform any of the operations of said assembly.

In an embodiment, the assembly comprises a proximity sensor 412, 422 coupled with the optical cardiac activity sensor 410, 420, wherein the optical cardiac activity sensor 410, 420 is configured to activate and/or deactivate responsive to measurements by the proximity sensor 412, 422. For example, if two sensors 410, 420 are used (i.e. one at each handle), there can be two proximity sensors 412, 422. However, if only one sensor 410 is used, only one proximity sensor 412 may be used. So, if the user places his/her hand at the handle, the proximity sensor 412 may activate the optical cardiac activity sensor 410. If the hand is removed, the sensor 410 may be deactivated. So, for example, if only one of the handles is used, the sensor at the other handle may not be activated unnecessarily, thus reducing amount of needed energy. However, it may also be possible that one proximity sensor (e.g. located at one of the handles) is configured to activate/deactivate both sensors. As noted above, there may be cases where the cardiac activity is measured using two or more sensors situated at the same or different handles. For example, the first optical sensor 410 may be situated at a first handle and the second optical sensor 420 at a second handle. Let us then discuss more about the sensor fusion with reference to FIG. 5, wherein the sensor fusion utilizes cardiac activity measurements performed by two or more cardiac activity sensors (e.g. one or more optical sensors and/or two or more electrodes).

Figure 5:
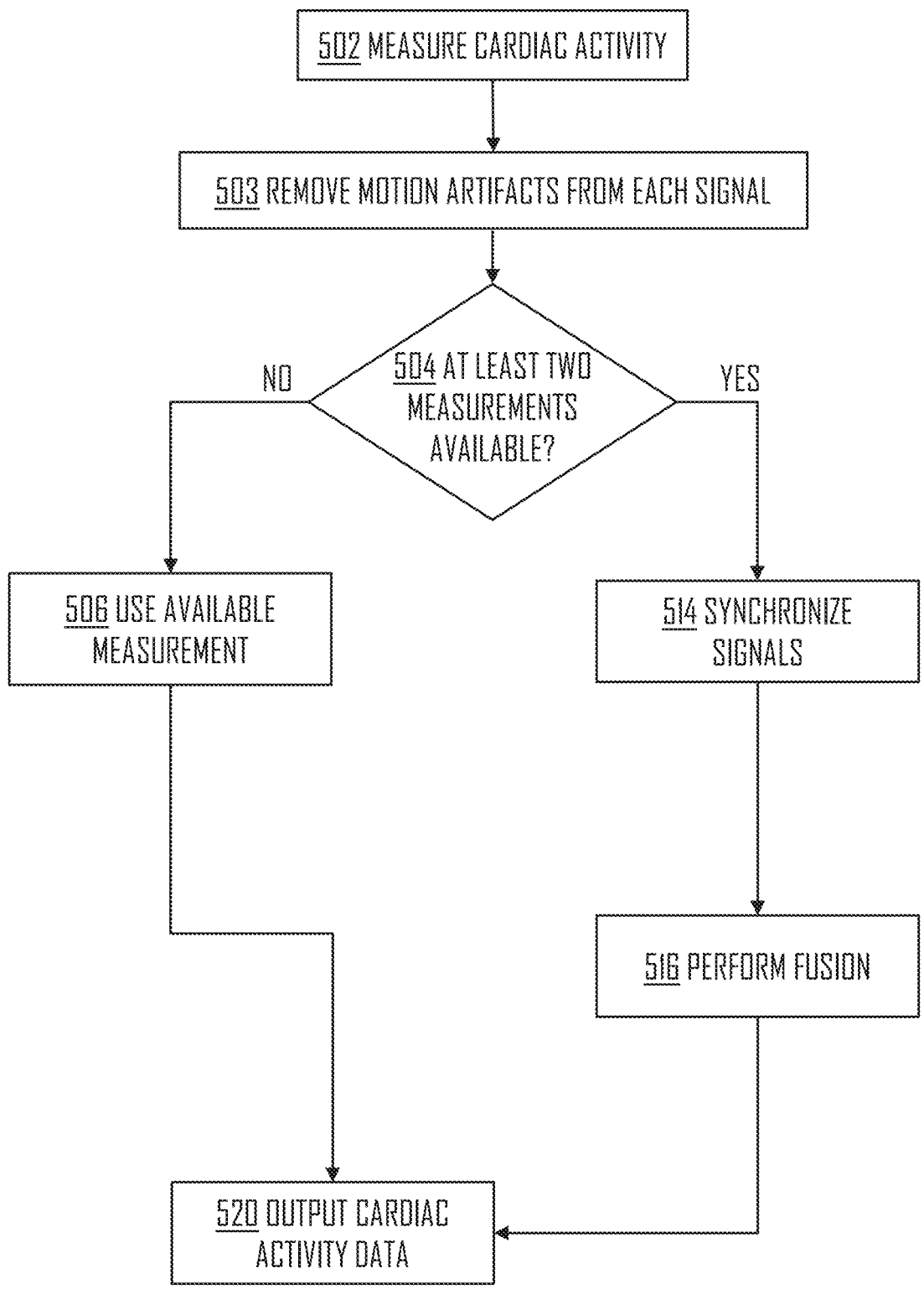
FIG. 5 illustrates a flow diagram according to an embodiment.

Referring to FIG. 5, in block 502, the assembly measures cardiac activity of the user.

In block 503, motion artifacts are removed (or at least reduced) from each cardiac activity signal, for example, by utilizing the motion signals or motion data associated with respective measurement source (i.e. cardiac activity sensor). As explained above, the motion signal(s) or motion data may be obtained using motion circuitry (e.g. accelerometer and/or gyroscope), using bioimpedance measurement and/or using electromagnetic radiation based measurement (e.g. UV or IR reflection). This motion signal removal/reduction may be optional, but beneficial, and it can be performed for each obtained signal (e.g. for left hand signal and for right and signal)

In block 504, the assembly determines whether there are at least two measurement sources available (i.e. at least two cardiac activity signals). If no, the process continues to block 506. If yes, the process continues to block 514.

In block 506, the assembly utilizes the available measurement (i.e. only available signal) and in block 520 outputs the cardiac activity data (e.g. display to the user or transmit to external location).

In block 514, the different cardiac activity signals are synchronized (i.e. timewise). This synchronization may be optional, but beneficial.

In block 516, the sensor fusion is performed. It is noted that it is possible to run the proposed sensor fusion algorithm with only one signal active. However, the benefits may be obtained from sensor fusion if there is more than one cardiac activity signal available. Multiple sensor topology on a sports equipment (e.g. optical sensors at both handles) may give further benefits for the cardiac activity measurement. The main advantage may be that when a plurality of signals are available, combining them more robustness may be achieved. As described, preprocessing (e.g. block 503, 514) may take also place before the fusion of block 516. It is noted that the motion signals and/or motion data may additionally or alternatively be acquired using one or more multidimensional motion sensors (can be referred to as motion circuitry) (e.g. acceleration sensor and/or gyroscope). Regarding the synchronization in block 514, measurement obtained from the right hand may delayed due to a further distance from the heart. Although phase error may not be large it may be beneficial to be compensated to avoid inaccurate signal timing and spectrogram shifted in time.

So, for example, the assembly may comprise a first optical cardiac activity sensor 410 configured to be (or is) floatingly attached to a first handle of the sports equipment and to be in skin contact with a first hand of the user, and a second optical cardiac activity sensor 420 configured to be (or is) floatingly attached to a second handle of the sports equipment and to be in skin contact with a second hand of the user. Further, the CTRL 400 or some other processing device may receive measurements from both the first and second optical cardiac activity sensors 410, 420 and perform the sensor fusion of block 516 (and optionally but preferably steps 503, 514). The CTRL 400 may receive the measurements, for example, via wireless transmission (e.g. Bluetooth) from each sensor. Such can be beneficial, for example, if the sports equipment comprises skiing poles and the like which utilize physically separate entities. On the other hand, it is possible to utilize wired connection and transmission if the sports equipment is, for example, gym equipment such as a treadmill or the like.

In an embodiment, the CTRL 400 comprises sensor fusion software and/or hardware (e.g. CPU 430 may perform the sensor fusion closer to the handles and provide the data to the MPU 440 for further processing) to combine cardiac activity signals from plurality of sensors (e.g. one cardiac activity sensor at first handle and another at a second handle). Such may be beneficial, for example, when the proposed solution is used in a gym equipment.

In general, the sensor fusion software and/or hardware may combine measurement data acquired from at least two cardiac activity sensors (e.g. block 516). Sensor fusion may be especially suitable for sports equipment based measurement in which the cardiac activity may be measured from more than one handle (e.g. skiing poles or handle bar based measurement). That is, it may be beneficial to have sensors at both handles if the sports equipment utilizes two handles. Thus, the measurement may be continuous even if user rests his/her other arm or uses a water bottle or some other equipment with his other arm, or can use or have only one arm. It can be possible to use only one of the signals, but it is even better to use sensor fusion which may take into account all available signals. Hence, the measurement may be as accurate as possible without a need for compromising. It is even possible that the sensor fusion algorithm utilizes only one of the signals if the other(s) are too noisy or if they are not available. That is, the sensor fusion algorithm may work with different number of signals (i.e. one or more).

There may be different ways to perform the sensor fusion of plurality of cardiac activity sensors. According to a first embodiment, the cardiac activity signals from plurality of sensors are combined by weighting the signals in proportion to their variances. So, for example, if we have two signals (i.e. one measured from left hand and the other from right hand), the fusion can be expressed as follows:

$$Yfusion = k1*Xml(t-Td) + k2*Xmr(t),$$

where
k1+k2=1,
Tml=The time for the pulse to reach the left hand,
Tmr=The time for the pulse to reach the right hand,
Tmr>Tml,
Td=Tmr−Tml, an additional delay of the signal from the left hand to synchronize the pulse wave with the signal of the right hand of the user, Xml signal measured from the left hand, and Xmr signal measured from the right hand.

It is noted that it takes time for a blood pulse to travel from heart to hand, and that time may be different between heart-to-left-hand (i.e. Tml) and heart-to-right-hand (i.e. Tmr). Hence, the time difference Td denoted as additional delay can be calculated, wherein Td can be used to synchronize the signals with each other.

k1 and k2 are weighting factors and can be determined by estimating the noise in the signals. So, for example, if signal from left hand is noisier than signal from the right hand (or not at all available), the equation weights the right hand signal more (or uses only the right hand signal), thus providing a better quality fusion signal Yfusion. The additional delay Td can be estimated by cross correlating the left and right hand signals. The Yfusion signal (can be referred to as fusion cardiac activity signal) may further be processed (e.g. by CTRL 400) to provide one or more cardiac activity metrics, such as HRV, heart rate, HBI, to name a few examples (e.g. as output in block 520). So, the cardiac activity signals from left and right hand are synchronized (e.g. block 514) and combined by sum function that weights the different signals based on their noise. Noise can be estimated by using one or more noise measuring techniques known in the art of signal processing. In one example embodiment, noise refers to and/or is caused by the amount of motion interference (i.e. motion artifacts) in the cardiac activity signals (see block 503 in which it is tried to be removed/mitigated). Additionally or alternatively, the quality of contact can be used to determine the weighting factors k1 and k2. The better the quality compared to the other, the greater the weighting factor. So, in general, the quality of contact determined, for example, using bioimpedance measurement and/or motion measurement (e.g. IR and/or UV light) can be used to weight different signals in a sensor fusion algorithm/process. The better the determined quality, the greater the weighting factor.

According to another embodiment, the sensor fusion utilizes various estimators such as a Kalman filter. This can be done for example using a Recursive adaptive estimator to compensate for varying noise sources. A Kalman filter is an optimal linear quadratic state estimator that can optimally combine multiple signal measurements in colored noise.

In an embodiment, the metric characterizing cardiac activity of the user comprises HRV, HBI and/or heart rate. Hence, the sensor fusion (e.g. Yfusion signal) may be used to calculate said HRV, HBI and/or heart rate.

Figure 6A:
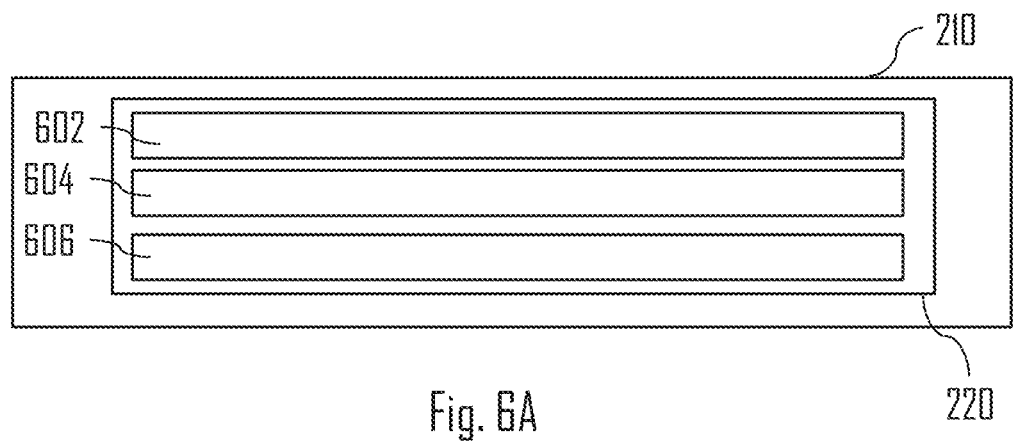
FIGS. 6A, 6B, 6C, 6D, 6E, 6F, 6G, and 6H illustrate embodiments related to use of elongated tubes for conveying electromagnetic radiation to measurement area utilizing total reflection.

FIGS. 6A, 6B, 6C, 6D, 6E, 6F, 6G, and 6H illustrate some embodiments in which additionally one or more light tubes are utilized to further enhance optical cardiac activity measurement from handle(s) of the sports equipment 108. It is noted that in some embodiments, the light tube(s) can be used without the floating attachment (i.e. a rigid attachment can be used). However, it is beneficial to use both to obtain even better measurement results. Referring to FIGS. 6A (top view) and 6B (view from the end of the handle), the handle 210 and optical cardiac activity sensor 220 are shown (not drawn in FIG. 6B). The optical cardiac activity sensor 220 further comprises at least one elongated tube 602, 604, 606 into which electromagnetic radiation is directed from at least one light emitting element of said sensor 220, the at least one elongated tube 602, 604, 606 configured such that the electromagnetic radiation is totally reflected (or at least substantially) inside said tube when said tube is in contact with air-interface, and such that when body tissue is placed in contact with said tube at least some of said electromagnetic radiation escapes said tube at the area of the contact.

Similar tube can be used for the detector. That is, the electromagnetic radiation may penetrate into the tube at an area of body tissue contact, and further totally reflect once inside the tube and eventually reach the detector. From the alterations, cardiac activity signal and/or motion signal can be produced and processed as described above, for example. Hence, in an embodiment, the optical cardiac activity sensor 220 comprises at least one first tube 632 for conveying electromagnetic radiation into the body tissue and at least one second tube 642 for receiving electromagnetic radiation from the body tissue, the at least one first tube 632 operationally connected with the at least one electromagnetic radiation emitting element 630 and the at least one second tube 642 operationally connected with the at least one electromagnetic radiation detector 640 of the optical cardiac activity sensor. The emitting elements 630 may be the elements 282 and the detector elements may be the detector 284, for example. So, for example, there can be one tube for visible light and another for UV/IR radiation, and further one or more tubes for each used detector. Different options are numerous and may vary between implementations.

The elongated tube 602, 604, 606 may thus comprise one or more tubes 632 and one or more tubes 642. Material of the tube may comprise glass, optic glass and/or plastics which is selected such that the needed total reflection (meaning total internal reflection) is achieved. It is known in the art of physics and optics that total reflection is dependent upon material refractive index and critical angle. Based on this knowledge, the tube 632 and the emitting element 630 and/or the tube 642 and the detector can be arranged and dimensioned such that the needed total reflection is acquired.

Figure 6B:
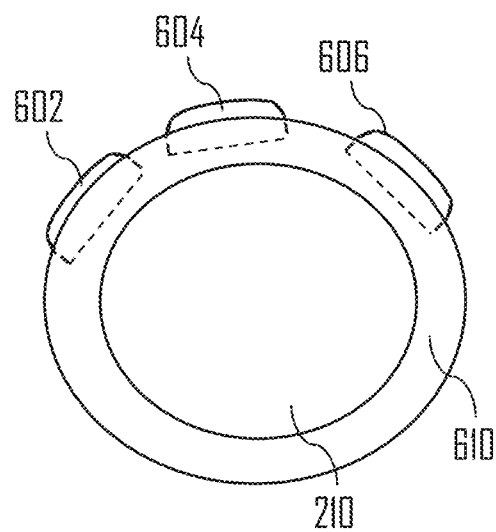
Figure 6C:
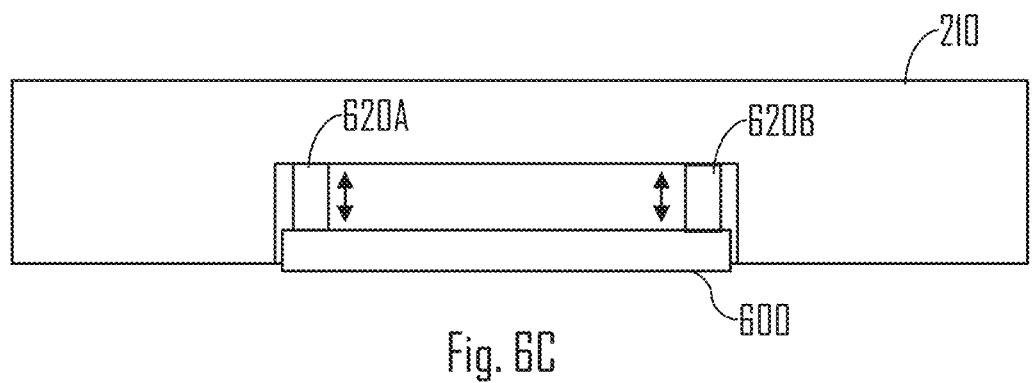
Figure 6D:
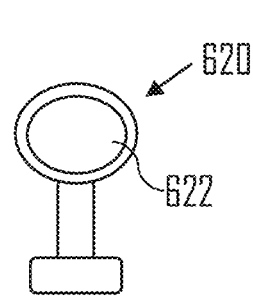
Figure 6E:
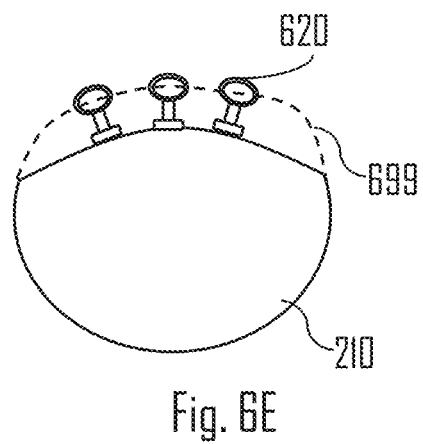

Referring now to FIG. 6B, in an embodiment, the assembly comprises a frame 610 configured to be coupled with the handle 210. The frame 610 may at least partially or fully embed the tube(s) 602, 604, 606 as shown in the Figure. For example, the frame 610 may at least partially encircle handle 210. For example, the frame 610 may comprise elastic material such that it enables/enhances the floating attachment. The frame 610 may, for example, be a plastic frame. Hence, it is not necessarily elastic. If the tube(s) 602, 604, 606 are fully embed inside the frame 610 (thus enabling easy attachment to the handle 210), the material of the frame 610 may be substantially optically invisible such that the light, IR and/or UV may travel from the tubes 602, 604, 606 to the skin of the user when the refractive index is changed as described. It is noted that tube(s) 602, 604, 606 may form at least part of the measuring head 222. Thus, they may need to be placed such that when the handle 210 is gripped, the tubes come in contact with body tissue (e.g. skin). Hence, the refractive index of body tissue causes the optical path to change, e.g. light can penetrate to the skin as it may not totally reflect anymore at the body tissue contact area. Examples of this are shown in FIGS. 6F, 6G, and 6H.

Figure 6F:
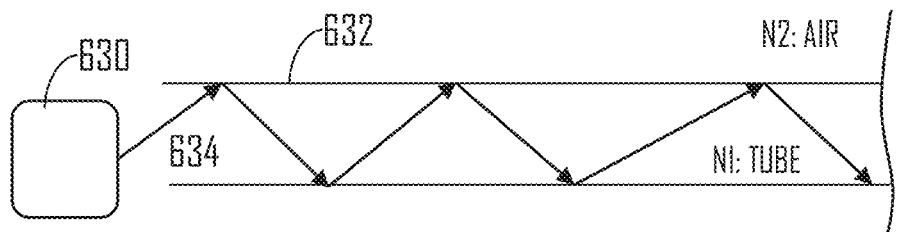
Figure 6G:
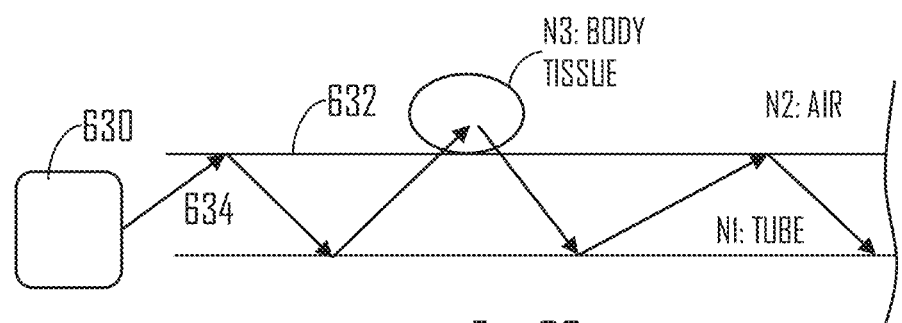

In FIG. 6F, light 634 (light is used as an example, but can be something else, such as IR or UV) is emitted by the element 630 into the tube 632. As noted above, N2: air (i.e. refractive index of air) and N1: tube (i.e. refractive index of tube 632) are such at certain angels the light 634 totally reflects and does not escape the tube. Situation changes in FIG. 6G as body tissue (e.g. finger) is placed in contact with the tube 632. Hence, the light may escape the tube 632 as refractive index changes to N3: body tissue (i.e. refractive index of body tissue, e.g. skin), and penetrate into the skin (depending on the frequency and wavelength of the radiation can also bounce right back).

Figure 6H:
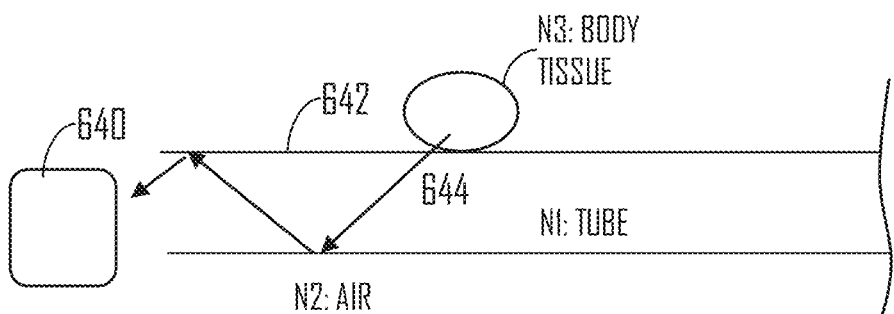

In FIG. 6H it is shown how the light 644 can be obtained back to the tube 642 and further reflected to the detector 640. So, for example, the body tissue receives the light 634 at contact area with the tube 632. At least some of said light 634 either bounces at an angle (e.g. IR or UV) or penetrates into the body tissue and travels to a different location(s). Either way the light 634 changes into light 644 (change may mean alterations and/or bouncing) and travels to a contact area with the tube 642. From the contact area, the light may penetrate into the tube 642 and eventually can be detected by the detector 640.

FIGS. 6C, 6D, and 6E show one example how the tube(s) 602, 604, 606 can be floatingly attached to the handle 210. In these figures, tube 600 refers to any of tubes 602, 604, 606. So, one option may be to use elastic holders 620. For example, two elastic holders 620A, 620B can be used arranged at different ends or end areas of the tube 600. Hence, an elastic frame 610 is not necessarily needed or may be a casing, such as a plastic casing, for the tubes 602, 604, 606 (see FIG. 6B). The elastic holder 620 may be a rubber holder, for example. The tube 600 can be fitted through or in an opening 622 such that the holder 620 may tightly hold the tube 600.

Looking at FIG. 6E, we can see that there can be plurality of tubes each assembled with the described holders 620 (e.g. two holders 620 for each tube). The dotted line 699 may represent outline of the handle 210. Hence, the holders 620 may be at least partially embedded into the handle 210. For example, as shown in FIG. 6C, the holders 620A, B may be arranged to be in a recess of the handle 210. Thus, the tube 600 may be placed such that it forms at least a part of the outer wall of the handle 210.

In more general terms, the elongated tube 600, 602, 604, 606, 632, 642 may refer to a tube that elongates parallel to the handle bar 210 or in the same direction as the handle bar, i.e. longitudinally with respect to the handle 210. Further, the tube 600 may be located on/at the surface of the handle bar 210. Thus, as explained, the tube may form a part of the handle 210, in some cases even substantial part of the handle 210. For example, the length (i.e. elongation direction) of the tube 600 may be about 10-15 centimeters (cm). So, for example, the elongation of the tube may be about width of a hand of an average person. So, the elongation of the tube may mean length of the tube.

According to an aspect there is provided a handle 210 (or handle bar 210) comprising the cardiac activity measurement assembly described above. In an embodiment, there is provided an arrangement comprising a plurality of said handles 210. For example, each may be connected to the CTRL 400, for example. Such arrangement may additionally comprise at least some or all elements described with respect to FIG. 4. It is also possible to provide such arrangement without the handle(s). In such case the arrangement may be coupled with the handle(s) by the user, for example.

In an embodiment, the sports equipment 108 comprises gym equipment such as a treadmill, a cross-trainer, a bike or a rowing machine.

It is further noted that at least in some embodiments, the floating attachment is such that the measuring head 222 of the sensor 220 initially extends above outer wall of the handle 210. Hence, when user grips the handle 210, his/her hand may touch the measuring head 222 (with or without the tubes 600). Now, as the floating attachment enables the sensor to move to reduce pressure on said measuring head 222, the sensor 220 may move towards the recess (e.g. cavity 212). Once the user stops the gripping, the sensor may move back to its initial position.

It is also noted that the method steps and/or operations described above may be performed or caused to be performed by one or more entities of the arrangement. One example of such is CTRL 400 or its specific parts (e.g. CPU 430, MPU 440).

It was disclosed how the presented solution and its embodiments can be used to provide accurate cardiac activity information, such as HRV, HBI and heart rate, to the user. Additionally or alternatively, in an embodiment, the CTRL 400 is further configured to calculate one or more physiological parameters (e.g. health index) from the measurements. Said physiological parameter(s) may be used by the user and/or coach to optimize training of the user, for example. For example, if more than one cardiac activity signal is available, pulse transit time (PTT) may be calculated and/or outputted. From PTT different parameter(s), such as blood pressure, can be calculated and outputted, for example, by the CTRL 400. More than one cardiac activity signal may be obtained, e.g. from both hands using optical measurement and/or from combination of optical measurement and electrode based measurement (can be referred to as contact heart rate (CHR). It may be especially beneficial to measure the PTT using optical measurement from hand and CHR measurement. That is because a blood pulse takes time to travel from heart to hand and the optical measurement is performed at the hand area. However, using CHR enables more instant measurement as the electrode based measurement may measure the blood pulse without (or with very little) delay. This may be because one electrode may be situated at one handle and the other at the other handle, and thus the measurement may be between said handles which may enable measurement of the blood pulse generation time (i.e. when heart contracts and generates the blood pulse). So, the additional benefit of using the optical cardiac activity measurement may actually be the delay observed at such measurement which may enable other parameters, such as blood pressure, to be measured efficiently when combined with, for example, CHR measurement.

It may even be possible to measure PTT and/or blood pressure utilizing two optical cardiac activity sensors (e.g. PPG sensors). This is because distance x from heart to left hand is different than distance y from heart to right hand. Difference between x and y can be denoted as distance d, and d is constant. Hence, as noted above, the time the blood pulse takes to travel distance d can be calculated. As d is constant, the blood pulse speed may be estimated which is proportional to blood pressure. Hence, it is possible to calculate blood pressure.

As used in this application, the term motion sensor or motion circuitry may refer to one or more accelerometers and/or one or more gyroscopes used individually or in combination (e.g. sensor fusion) to measure motion. Particularly, in the present solution the motion measurement may refer to measuring motion between the head 222 and the body tissue to detect motion artefacts which may cause the cardiac activity signals to be unusable or of poor quality. The motion measurement, in general, may comprise one or more of the disclosed techniques: motion sensor measurement, bioimpedance measurement, UV/IR/reflection measurement. Using more than one of said techniques may further enhance the accuracy of the motion artefact detection and removal from the cardiac activity signal(s).

Performing the motion measurement utilizing motion sensors (e.g. accelerometer and/or gyroscope) may provide additional data about movement of the hand of the user. Hence, it is possible to reveal/determine relative motion between the measuring head 222 and the hand of the user.

Hence, for example, the motion sensor data may be used, by the CTRL 400, to detect a movement pattern and used the movement pattern to filter interference (e.g. motion artefacts) from the cardiac activity data/signal. The movement pattern could be, for example, cadence observed during cycling which is caused by the grip of the user changing with certain interval. For example, grip may change during each pedaling cycle (e.g. caused by balance shift from left to right and back). Hence, as noted, the motion measurement using the motion sensors may not be solely restricted to measuring motion of the measuring head 222.

It is further noted that the floating attachment may refer to elastic attachment of the sensor 220 or sensors to handle(s) of the sports apparatus 108.

According to an embodiment, the sensor 220 is floatingly attached to some other entity than sports apparatus 108. For example, steering wheel could be one example in order to measure cardiac activity of a user operating a vehicle.

It is further noted that gripping the handle 210 may also comprise obvious alternatives such as leaning on the handle or handles 210 (e.g. bicycle).

It is further noted that the cardiac activity measurement assembly may be referred to as an arrangement or a system.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with the Figures may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of the Figures or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of the Figures, or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with the Figures may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:
1. A cardiac activity measurement assembly for a sports equipment, said assembly comprising:
   an optical cardiac activity sensor configured to measure cardiac activity of a user;
   a handle comprising a cavity configured to receive the optical cardiac activity sensor;

an attachment element configured to floatingly attach the optical cardiac activity sensor in the cavity of the handle to enable entry of the optical cardiac activity sensor into the cavity, and to reduce pressure on a measuring head of said optical cardiac activity sensor caused by a skin contact between said measuring head and at least one finger or a palm of the user when gripping the handle;

a guide element configured to reduce or prevent tilting of the measuring head due to force applied on the measuring head of said optical cardiac activity sensor; and a plurality of electrodes situated at the measuring head of the optical cardiac activity sensor and configured to measure motion between the measuring head and a body tissue of the user.

2. The assembly of claim 1, wherein the attachment element comprises at least one spring.

3. The assembly of claim 1, wherein the attachment element comprises a hydraulic control system.

4. The assembly of claim 1, wherein the attachment element comprises elastic shock-absorbing material.

5. The assembly of claim 1, wherein the optical cardiac activity sensor is configured to operate with electromagnetic radiation of at least two different wavelengths.

6. The assembly of claim 5, wherein the optical cardiac activity sensor is configured to emit a first electromagnetic radiation having a first wavelength for measuring the cardiac activity of the user and a second electromagnetic radiation having a second wavelength for measuring motion between the measuring head and a body tissue of the user, and wherein the first wavelength is such that the first electromagnetic radiation penetrates deeper into the body tissue compared with the second electromagnetic radiation.

7. The assembly of claim 6, wherein the first electromagnetic radiation comprises visible light and the second electromagnetic radiation comprises ultraviolet and/or infrared radiation.

8. The assembly of claim 6, further comprising a processing circuitry configured to obtain motion data indicating the motion between the measuring head and the body tissue of the user and cardiac activity data from the optical cardiac activity sensor, and to process the cardiac activity data based on the motion data in order to reduce an effect of motion artefacts on the cardiac activity data.

9. The assembly of claim 6, wherein the motion measurements are for determining quality of said skin contact.

10. The assembly of claim 1, further comprising at least one motion sensor configured to measure motion between the measuring head and a body tissue of the user.

11. The assembly of claim 1, further comprising a proximity sensor coupled with the optical cardiac activity sensor, wherein the optical cardiac activity sensor is configured to activate and/or deactivate responsive to measurements by the proximity sensor.

12. The assembly of claim 1, wherein the optical cardiac activity sensor comprises at least one elongated tube into which light is directed from at least one light emitting element of said sensor, the at least one elongated tube configured such that the light is totally reflected inside said tube, and such that when body tissue is placed in contact with said tube at least some of said light escapes said tube at the area of the contact.

13. The assembly of claim 12, wherein the optical cardiac activity sensor comprises at least one first tube for conveying light into the body tissue and at least one second tube for receiving light from the body tissue, the at least one first tube operationally connected with the at least one light emitting element and the at least one second tube operationally connected with the at least one light detector of the optical cardiac activity sensor.

14. The assembly of claim 1, wherein the optical cardiac activity sensor is a first optical cardiac activity sensor configured to be in skin contact with a first hand of the user, the assembly further comprising:

a second optical cardiac activity sensor configured to be floatingly attached to a second handle of the sports equipment and to be in skin contact with a second hand of the user; and a sensor fusion element for receiving measurements from both the first and second optical cardiac activity sensors and for combining said measurements into a metric characterizing cardiac activity of the user.

\* \* \* \* \*